United States Patent
Goossen et al.

(10) Patent No.: US 6,531,607 B2
(45) Date of Patent: Mar. 11, 2003

(54) IMMOBILIZED PALLADIUM COMPLEXES

(75) Inventors: Lukas Goossen, Mühlheim (DE); Martin Hendrix, Köln (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/862,161

(22) Filed: May 21, 2001

(65) Prior Publication Data

US 2001/0056190 A1 Dec. 27, 2001

(30) Foreign Application Priority Data

May 24, 2000 (DE) .................................. 100 25 623

(51) Int. Cl.$^7$ .............................. C07F 9/80; C07F 9/06
(52) U.S. Cl. ...................................... 548/103; 548/112
(58) Field of Search ................................ 548/103, 112

(56) References Cited

U.S. PATENT DOCUMENTS 5,576,460 A  11/1996  Buchwald et al. .......... 564/386

OTHER PUBLICATIONS

K. Weissermel et al, Industrial Organic Chemistry (month unavailable) 1993 2$^{nd}$ edition, pp. 370–373, 13.3.2. Aniline.
Organic Letter, Nolan et al, vol. 1, No. 8, (month unavailable) 1999, pp. 1307–1309, General and Efficient Catalytic Amination of Aryl Chlorides Using a Palladium/Bulky Nucleophilic Carbene System, Jinkun Huang, Gabriella Grasa, and Steven P. Nolan. 1994.
J. Blumel, Inorg. Chem. 33 (month unavailable) pp. 5050–5056, 1994 Reactions of Phosphines with Silica: A Solid–State NMR Study. Janet Blumel.
F.R. Hartley, Supported Metal Complexes, D. Reidel Publishing Company, Dordrecht, Boston Lancester, Tokyo (month unavailable) 1985, pp. 170–174, Chapter 6, Hydrogenation.
Chem. Ber. (month unavailable) 1996, 129. pp. 459–463, 8–Quinolylcyclopentadienyl, a Ligand with a Tailored Fit for Chelate Complexes, Markus Enders, Ralph Rudolph, and Hans Pritzkow.
Chem. Eur. J. 2(12) (month unavailable) 1996, pp. 1627–1635, Wolfgang A. Hermann et al, "Heterocyclic Carbenes: [+]A High–Yielding Synthesis of Novel, Functionalized N–Heterocyclic Carbenes in Liquid Ammonia".
J. Organomet. Chem., 547 (month unavailable) 1997, pp. 357–366, Wolfgang A. Hermann et al, "Functionalized imidazoline–2–ylidine complexes of rhodium and palledium".
Agew Chem., 110 (month unavailable) 1998, pp. 2155–2177, John F. Hartwig Übergangsmetallkatalysierte Synthese von Arylaminen und Arylethern aus Arylhalogeniden und —triflaten: Anwendungen und Reaktionsmechanismus.
Organic Letters, vol. 2, No. 10, (month unavailable) 2000, pp. 1423–1426, Shaun R. Stauffer et al, High Turnover Number Rapid, Room–Temperature Amination of Chloroarenes Using Saturated Carbene Ligands.

Primary Examiner—Joseph K. McKane
Assistant Examiner—Golam M. M. Shameem
(74) Attorney, Agent, or Firm—Godfried R. Akorli; Diderico van Eyl

(57) ABSTRACT

The invention relates to immobilized palladium complexes, to a process for their preparation, to their use as catalysts and to a process for the preparation of arylamines using immobilized palladium complexes.

4 Claims, No Drawings

IMMOBILIZED PALLADIUM COMPLEXES

The invention relates to immobilized palladium complexes, to a process for their preparation, to their use as catalysts and to a process for the preparation of arylamines using the immobilized palladium complexes.

Arylamines, especially substituted anilines, are of great industrial importance as precursors for dyestuffs, fine chemicals, pharmaceuticals and agrochemicals. Arylamines are generally prepared on the industrial scale by the nitration of an appropriate aromatic compound, followed by hydrogenation. As nitrations are carried out under drastic reaction conditions, a large number of complex substituted arylamines cannot be prepared satisfactorily in this way, if at all.

Arylamines can also be prepared by the ammonolysis of phenols and chlorobenzenes (K. Weissermel et al., Industrial Organic Chemistry, 1993, 2nd edition, VCH Verlagsgesellschaft, Weinheim, 370–373). Again, because of its drastic reaction conditions, this procedure is unsuitable for the preparation of substituted arylamines.

U.S. Pat. No. 5,576,460 describes a process for the preparation of arylamines by reacting metal amides, prepared in situ, with amines using palladium complexes carrying phosphine ligands. The disadvantage of this process is that the phosphine ligands required for this purpose are normally expensive, air-sensitive and difficult to handle. The palladium complexes produced therefrom in situ are also air-sensitive and susceptible to degradation reactions.

Nolan et al., Organic Letters Vol. 1, No. 8, 1999, 1307–1309, describe the preparation of arylamines using palladium catalysts carrying heterocyclic carbenes as ligands. In comparison with phosphine ligands, heterocyclic carbenes have a high thermal and chemical stability. However, one disadvantage of the palladium catalysts used by Nolan et al. is that they have to be removed from the reaction mixture when the reaction has ended, which is costly. Another disadvantage is that the catalyst cannot be recycled, i.e. re-used in another reaction.

Surprisingly, immobilized palladium complexes have now been found which are distinguished by their ease of preparation, their high thermal stability and their insensitivity to oxygen and moisture. The complexes according to the invention have a high activity and selectivity and can preferably be used as catalysts for the preparation of arylamines. When the reaction has ended, the catalysts can easily be separated from the reaction mixture and used in another reaction without loss of activity.

The complexes according to the invention are supported compounds of formula (I):

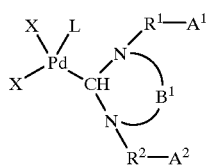

(I)

in which
X is halogen, trifluoromethanesulphonate, acetylacetonate or acetate,
L is a radical of the formula $P(D)_3$, D being alkyl, cycloalkyl, aryl, aralkyl, alkylaryl or heteroaryl, or
  a radical of the formula $N(E)_2$, E being alkyl, cycloalkyl, aryl, aralkyl, alkylaryl or heteroaryl, or a radical of formula (II):

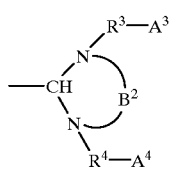

(II)

in which
$B^1$ and $B^2$ are identical or different and are a radical to complete a heterocycle, especially

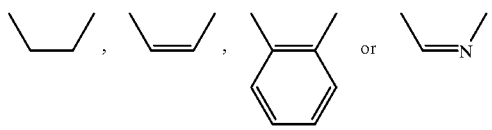

$R^1$–$R^4$ are identical or different and are a divalent radical from the group comprising alkyl, cycloalkyl, aryl, aralkyl and alkylaryl, each of which is optionally substituted by COO—($C_1$–$C_4$-alkyl), O($C_1$–$C_4$-alkyl) or $CONH_2$, and
$A^1$–$A^4$ are identical or different and are hydrogen or a chemical bond from the group comprising —CONH—, —CO—O—OC—, —COO—, —O— and

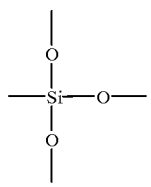

via which the complex is bonded to the support, with the proviso that at least one A is other than hydrogen.

The terms used above are defined as follows:
"Halogen" denotes F, Cl, Br or I.
"Alkyl" denotes linear or branched —$C_1$–$C_{12}$-alkyl, for example methyl, ethyl, propyl, isopropyl, butyl, sec-butyl, tert-butyl, pentyl, neopentyl, hexyl, heptyl, isoheptyl, 2-ethylhexyl or octyl.
"Cycloalkyl" denotes —$C_3$–$C_8$-cycloalkyl, for example cyclopropyl, cyclobutyl, cyclopentyl, cyclohexyl, cycloheptyl or cyclooctyl.
"Aryl" denotes —$C_6$–$C_{14}$-aryl, for example phenyl, naphthyl or biphenyl.
"Aralkyl" denotes —$C_1$–$C_{12}$-alkyl-$C_6$–$C_{14}$-aryl, the free valency being on the alkyl moiety, for example phenylmethyl, phenylethyl, naphthylmethyl, naphthylethyl, diphenylmethyl or triphenylmethyl.
"Alkylaryl" denotes —$C_6$–$C_{14}$-aryl-$C_1$–$C_{12}$-alkyl, the free valency being on the aryl moiety, for example tolyl, ethylphenyl, xylyl, methylnaphthyl or ethylnaphthyl.
"Heteroaryl" denotes unsaturated rings having 5 or 6 atoms and containing one or two oxygen atoms and sulphur atoms and/or one to four nitrogen atoms, with the proviso that the total number of heteroatoms is four or less, for example furan, thiophene, pyridine, pyrrole or imidazole, or bicyclic rings in which the 5- or 6-membered rings defined above are fused to a benzene or pyridine ring, for example purines, benzopyran or benzimidazole.

The complexes according to the invention are preferably supported compounds of formula (I) in which X is halogen,
L is a radical of the formula P(D)$_3$, D being a radical from the group comprising cyclohexyl, phenyl, naphthyl and tolyl, or a radical of formula (II):

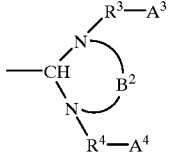
(II)

in which
B$^1$ and B$^2$ are identical or different and are

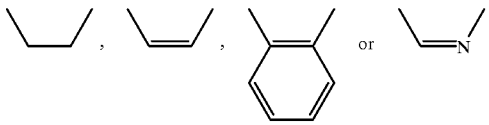

R$^1$–R$^4$ are identical or different and are a divalent radical from the group comprising alkyl, cycloalkyl, aryl, aralkyl and alkylaryl, each of which is optionally substituted by COO—(C$_1$–C$_4$-alkyl), O(C$_1$–C$_4$-alkyl) or CONH$_2$, and
A$^1$–A$^4$ are identical or different and are hydrogen or a chemical bond from the group comprising —CONH—, —CO—O—OC—, —COO—, —O— and

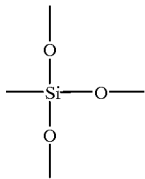

via which the complex is bonded to the support, with the proviso that at least one A is other than hydrogen and the support is selected from the group comprising inorganic supports and polymeric supports.

The complexes according to the invention are particularly preferably compounds of formula (I) in which
X is I,
L is

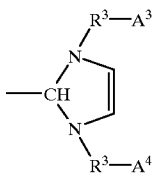

B$^1$ is

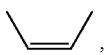

R$^1$ and R$^3$ are identical and are a divalent radical —(C$_1$–C$_6$-alkyl)-, preferably —CH$_2$—,
R$^2$ and R$^4$ are identical and are a divalent radical —(C$_1$–C$_6$-alkyl)-, preferably —(CH$_2$)$_3$,
A$^1$ and A$^3$ are identical and are hydrogen, and A$^2$ and A$^4$ are identical and are a chemical bond from the group comprising —CONH—, —CO—O—OC—, —COO—, —O— and

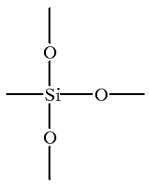

and the support is an inorganic support from the group comprising silica gel, magnesium oxide and aluminium oxide, or a polymeric support from the group comprising polyester, polyether, polyethylene, polypropylene and polystyrene.

Very particularly preferred supports are functionalized polystyrenes crosslinked with divinylbenzene, such as those conventionally used in solid phase peptide chemistry or for solid phase synthesis.

The complexes according to the invention can be prepared in situ or separately. This can be done by first fixing the ligands to the support. The fixed ligands can then be converted in situ or separately to the complexes according to the invention.

Another possibility for separate preparation is first to prepare the free complex from ligands and Pd compound and then to fix it to the support in order to prepare the complexes according to the invention.

The invention further relates to a process for the preparation of compounds of formula (I) which is characterized in that compounds of formulae (III) and (IV):

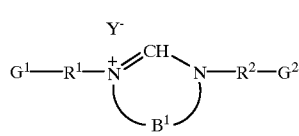
(III)

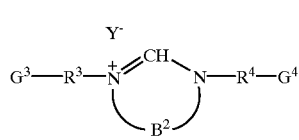
(IV)

in which
B$^1$ and B$^2$ are identical or different and are a radical to complete a heterocycle, especially

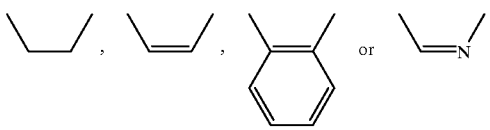

R$^1$–R$^4$ are identical or different and are a divalent radical from the group comprising alkyl, cycloalkyl, aryl, aralkyl and alkylaryl, each of which is optionally substituted by COO—(C$_1$–C$_4$-alkyl), O(C$_1$–C$_4$-alkyl) or CONH$_2$,
G$^1$–G$^4$ are identical or different and are hydrogen, COOH, CO—O—CO(C$_1$–C$_4$-alkyl), COO(C$_1$–C$_4$-alkyl), COCl, CO(C$_1$–C$_4$-alkyl), COH, NH$_2$, NH(C$_1$–C$_4$-alkyl), OH, Si(O—C$_1$–C$_4$-alkyl)$_3$ or OCN, with the proviso that at least one G is other than hydrogen, and Y is an anion from the group comprising Cl, Br, I, $C_1$–$C_4$-alkylsulphonate, $C_6$–$C_{14}$-arylsulphonate, hexafluorophosphate and tetrafluoroborate, or compounds of formulae (III) and $P(D)_3$, or compounds of formulae (III) and $N(E)_2$, are reacted with Pd(II) compounds in the presence of a base, and the reaction product, a Pd/N-heterocyclic complex, is immobilized on a support which has groups reactive towards G, other than hydrogen. The above-described process according to the invention will be called synthesis variant A hereafter.

The invention further relates to a process for the preparation of compounds of formula (I) which is characterized in that compounds of formula (III) or compounds of formulae (III) and (IV) are immobilized on a support which has groups reactive towards G, other than hydrogen, and with Pd(II) compounds and—in the case where only compounds of formula (III) are immobilized on a support—with $P(D)_3$ or $N(D)_2$ in the presence of a base. The above-described process according to the invention is called synthesis variant B hereafter.

The compounds of formulae (III) and (IV) are preferably imidazoles, imidazolines, triazoles or benzimidazoles and particularly preferably imidazoles.

The compounds $P(D)_3$ are preferably those in which D is a radical from the group comprising cyclohexyl, phenyl, naphthyl and tolyl.

The Pd/N-heterocyclic complex is preferably prepared using compounds of formulae (III) and (IV) in which $R^1$–$R^4$ are identical or different and are a divalent radical from the group comprising —($C_1$–$C_6$-alkyl)—, —($C_6$–$C_{14}$-aryl)— and —($C_1$–$C_4$-alkyl-$C_6$-aryl)—, $B^1$ and $B^2$ are identical or different and are

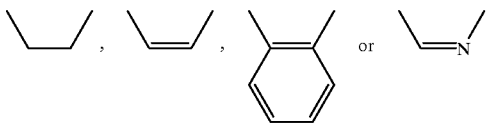

$G^1$ and $G^3$ are hydrogen, and $G^2$ and $G^4$ are identical or different and are COOH, CO—O—CO($C_1$–$C_4$-alkyl), COO($C_1$–$C_4$-alkyl), COCl, CO($C_1$–$C_4$-alkyl), $NH_2$, NH($C_1$–$C_4$-alkyl), Si(O—$C_2$–$C_4$-alkyl)$_3$, OCN or OH.

Particularly preferably, the compounds of formulae (III) and (IV) used are those in which $B^1$ and $B^2$ are

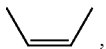

$R^1$ and $R^3$ are identical and are a divalent radical —($C_1$–$C_6$-alkyl)—, preferably —$CH_2$—, $R^2$ and $R^4$ are identical and are a divalent radical —($C_1$–$C_6$-alkyl)—, preferably —$(CH_2)_3$—, $G^1$ and $G^3$ are hydrogen, and $G^2$ and $G^4$ are identical and are COOH, CO—O—CO ($C_1$–$C_4$-alkyl), COO($C_1$–$C_4$-alkyl), COCl, $NH_2$, OH, Si(O—$C_1$–$C_4$-alkyl)$_3$ or OCN, preferably COO—($C_1$–$C_4$-alkyl).

The compounds of formulae (III) and (IV) can be prepared e.g. analogously to Herrmann et al., Chem. Eur. J. 2, No. 12, 1996, 1627–1636.

Each of the compounds of formulae (III) and (IV), $P(D)_3$ and $N(D)_2$ is preferably used in an amount of 0.6 to 4 equivalents, preferably of 0.8 to 3 equivalents and particularly preferably of 0.9 to 2 equivalents, based on the Pd(II) compounds.

The Pd(II) compounds used can be palladium acetate, halides, nitrate, carbonate, ketonate or acetylacetonate. It is preferred to use $Pd(OAc)_2$, $Pd(acac)_2$ or $PdCl_2$ and particularly preferred to use $Pd(OAc)_2$.

The bases used are preferably alkali metal and alkaline earth metal alcoholates such as lithium tert-butylate, sodium tert-butylate or potassium tert-butylate, and alkali metal and alkaline earth metal carbonates such as sodium carbonate or potassium carbonate. It is preferred to use alkali metal alcoholates or alkali metal carbonates and particularly preferred to use sodium tert-butylate or potassium carbonate. The base is preferably used in an amount of 0.5 to 2 equivalents, especially of 1 to 3 equivalents and particularly preferably of 1.2 to 2 equivalents, based on the Pd(II) compound.

The supports used are preferably inorganic supports or polymeric supports. Particularly preferably, the support is selected from the group comprising silica gel, magnesium oxide, aluminium oxide, polyester, polyether, polyethylene, polypropylene and polystyrene.

The processes according to the invention are preferably carried out in the presence of alkali metal iodides such as LiI, NaI, KI or CsI. It is preferred to use NaI or KI and particularly preferred to use NaI. The alkali metal iodides are preferably used in an amount of 2 to 6 equivalents, preferably of 3 to 5 equivalents, based on the Pd(II) compounds.

When the Pd/N-heterocyclic complexes are prepared by synthesis variant A, the reaction is preferably carried out in an inert solvent, preferably in a polar solvent and particularly preferably in tetrahydrofuran or ethanol.

The reaction takes place for example at temperatures of 0° C. to 100° C., preferably of 10° C. to 40° C. and particularly preferably of 18° C. to 25° C.

The reaction conventionally takes place with the exclusion of water, preferably under an inert gas such as nitrogen, argon or helium.

When the Pd/N-heterocyclic complexes are prepared by synthesis variant A, the abovementioned starting compounds can be placed in one reaction vessel. The solvent can then be added and the reaction mixture is preferably stirred for a few hours at room temperature. The progress of the reaction can be monitored by thin layer chromatography. When the reaction has ended, the solvent can be stripped off and the residue purified by column chromatography.

The Pd/N-heterocyclic complexes prepared by synthesis variant A are preferably immobilized on a support by reacting the Pd complex with the support in an amount corresponding to the desired subsequent loading of the support. If appropriate, the groups G of the Pd/N-heterocyclic complexes or the reactive groups of the support are activated with suitable reagents. For example, amino groups can be converted by compounds like triethylaluminium to more reactive diethylaluminium amides, or carboxyl groups can be converted to active esters or anhydrides. In the reaction, the functional groups of the carbene complex react with the reactive groups of the support to form a chemical bond. If appropriate, free reactive groups on the support which are still present after the reaction can be converted with suitable reagents to unreactive groups.

To immobilize the Pd/N-heterocyclic complexes on supports, it is possible to place the complex together with the support, optionally with the addition of activating reagents or condensing agents, in a solvent. In the case of polymeric supports, it is preferred to use solvents in which the polymeric support is in the swollen state. The reaction mixture is preferably mixed thoroughly, this thorough mixing preferably being effected by shaking because vigorous stirring can reduce the size of the supports. The reaction mixture is heated if appropriate. The progress of the reaction can be observed for example by solid phase FT-IR spectroscopy. When the reaction has ended, the support can be filtered off, washed and dried.

The immobilization of the Pd/N-heterocyclic complexes on inorganic supports can be carried out analogously to J. Blümel, Inorg. Chem. 33, 1994, 5050–5056.

The immobilization of the Pd/N-heterocyclic complexes on polymeric supports can be carried out analogously to F. R. Hartley, Supported Metal Complexes, D. Reidel Publishing Company, Dordrecht, Boston, Lancester, Tokyo 1985, 170–174.

It is preferred to immobilize the Pd/N-heterocyclic complexes on a polymeric support, preferably on polystyrene crosslinked with divinylbenzene and particularly preferably on a Merrifield resin, i.e. a chloromethylated polystyrene resin crosslinked with divinylbenzene, or on aminomethylated polystyrene crosslinked with divinylbenzene.

When synthesis variant B is used, the fixing to the support can be carried out analogously to the above description. The reaction of the supported compounds (III) and/or (IV) or $P(D)_3$ or $N(E)_2$ with Pd(II) compounds can also be carried out analogously to synthesis variant A.

The preparation of Pd/N-heterocyclic complexes with compounds of formulae (III) and $P(D)_3$ or $N(E)_2$ can be carried out analogously to Enders et al., Chem. Ber. 129, 1996, 459–463.

The compounds of formula (I) are suitable for example as catalysts for carbonylations, alkylations and hydrogenations and for the preparation of arylamines.

The compounds of formula (I) are preferentially suitable as catalysts for the preparation of arylamines.

The invention further relates to a process for the preparation of arylamines of formula (V):

$$Ar-NR^5R^6 \quad (V)$$

in which
Ar is phenyl, naphthyl, pyridyl, pyridazinyl, pyrimidyl, pyrazinyl, pyrryl, thiophenyl, furyl, imidazolyl, oxazolyl, isoxazolyl, thiazolyl or triazolyl, and the abovementioned radicals optionally carry one or more substituents from the group comprising $C_1$–$C_8$-alkyl, $C_3$–$C_8$-cycloalkyl, $C_1$–$C_8$-alkoxy, $C_1$–$C_8$-acyloxy, $C_6$–$C_{14}$-aryl, $C_6$–$C_{14}$-aryloxy, halogen, C(halogen)$_3$, $NO_2$, $NH_2$, $NH(C_1$–$C_8$-alkyl), $N(C_1$–$C_8$-alkyl)$_2$, NHCOR, NHCHO, NHCOOH, NHCOOR, OH, CN, COOH, CHO, $CO(C_1$–$C_8$-alkyl), $CO(C_6$–$C_{14}$-aryl), $CO_2(C_6$–$C_{14}$-aryl), $CO_2(C_1$–$C_8$-alkyl), $CONH_2$, $SO_3H$, $SO_2R$, SOR, $PO(C_6$–$C_{14}$-aryl)$_2$, $PO(C_1$–$C_8$-alkyl), $Si(C_1$–$C_8$-alkyl)$_3$ and heteroaryl, R being $C_1$–$C_4$-alkyl, and $R^5$ and $R^6$ independently of one another are hydrogen, $C_1$–$C_{12}$-alkyl, $C_3$–$C_8$-cycloalkyl or $C_6$–$C_{14}$-aryl, the abovementioned radicals optionally carrying one or more substituents from the group comprising $C_1$–$C_8$-alkyl, $C_3$–$C_8$-cycloalkyl, $C_1$–$C_8$-alkoxy, $C_1$–$C_8$-acyloxy, $C_6$–$C_{14}$-aryl, $C_6$–$C_{14}$-aryloxy, halogen, C(halogen)$_3$, $NO_2$, $NH_2$, $NH(C_1$–$C_8$-alkyl), $N(C_1$–$C_8$-alkyl)$_2$, NHCOR, NHCHO, NHCOOR, OH, CN, COOH, CHO, $CO(C_1$–$C_8$-alkyl), $CO(C_6$–$C_{14}$-aryl), $CO_2(C_6$–$C_{14}$-aryl), $CO_2(C_1$–$C_8$-alkyl), $CONH_2$, $SO_3H$, $SO_2R$, SOR, $PO(C_6$–$C_{14}$-aryl)$_2$, $PO(C_1$–$C_8$-alkyl), $Si(C_1$–$C_8$-alkyl)$_3$ and heteroaryl, R being $C_1$–$C_4$-alkyl, or together are a ring having up to 5 C atoms, it being possible for one C atom to be replaced by O or N, by reacting aryl compounds of formula (VI):

$$Ar-Q \quad (VI)$$

in which
Ar is as defined above, and
Q is halogen, trifluoromethanesulphonyl or toluenesulphonyl, with amines of formula (VII):

$$R^5R^6NH \quad (VII)$$

in which
$R^5$ and $R^6$ are as defined above,
or with

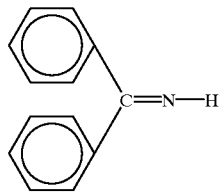

in the presence of bases, said process being characterized in that the reaction is carried out in the presence of compounds of formula (I).

Preferred aryl compounds of formula (VI) are mono- or disubstituted aromatic compounds. Examples of monosubstituted aromatic compounds are chlorobenzene, bromobenzene, iodobenzene, bromonaphthalene, bromopyridine or bromoimidazole. Preferred disubstituted aromatic compounds are those carrying substituents in the 1,3- or 1,4-positions, for example 4-nitrochlorobenzene, 4-methylchlorobenzene, 4-methoxychlorobenzene, 4-bromobenzonitrile, 4-bromobenzoic acid, 3-ethoxybromobenzene, 3-nitrobromobenzene or 3-methyliodobenzene.

Particularly preferred aryl compounds of formula (VI) are 1,3- or 1,4-disubstituted benzenes, for example 4-nitrobromobenzene, 4-nitrochlorobenzene, 3-methylchlorobenzene, 3-ethylbromobenzene or 4-bromobenzonitrile.

Preferred amines of formula (VII) are aromatic amines such as aniline, N-methylaniline or 2,4,6-trimethylaniline; heteroaromatic amines such as aminopyridine, aminopyrimidine or aminopyrrole; cyclic amines such as piperidine, piperazine, N-methylpiperazine or morpholine; aliphatic secondary amines such as N,N-diethylamine, N,N-dibutylamine; or aliphatic primary amines such as n-hexylamine.

Particularly preferred amines of formula (VII) are aromatic amines such as aniline, heteroaromatic amines such as aminopyridine or aminopyrimidine, and cyclic amines such as piperidine, piperazine, N-methylpiperazine or morpholine.

The amine of formula (VII) is preferably added in approximately stoichiometric amounts or in excess, based on the aryl compound of formula (VI). The amount of amine is preferably 1 to 3 equivalents and particularly preferably 1.2 to 2 equivalents.

The bases used are preferably alkali metal and alkaline earth metal hydroxides such as sodium hydroxide and potassium hydroxide, alkali metal and alkaline earth metal alcoholates such as lithium tert-butylate, sodium tert-butylate or potassium tert-butylate, alkali metal and alkaline earth metal carbonates such as potassium carbonate, alkali metal and alkaline earth metal amides, butyllithium, phenyllithium, sodium hexamethyldisilazide or lithium hexamethyldisilazide, preferably alkali metal alcoholates or alkali metal carbonates and particularly preferably sodium tert-butylate or potassium carbonate. The base is preferably used in an amount of 0.5 to 2 equivalents, especially of 1 to 3 equivalents and particularly preferably of 1.2 to 2 equivalents, based on the aryl compound of formula (VI).

The compounds of formula (I) can be used for example in amounts of 0.01 to 10 mol %, preferably of 0.05 to 5 mol % and particularly preferably of 0.1 to 2 mol %, based on the aryl compounds of formula (VI).

The compounds of formula (I) can be prepared separately or in situ. If the compounds of formula (I) are prepared in situ, the supported ligands can be reacted in the presence of Pd(II) compounds to give the compounds according to the invention, the preferred amount of supported ligands used being 1 to 5 equivalents, based on the Pd(II) compounds. The in situ preparation does not require a further addition of base.

The reaction can be carried out with or without a solvent. If the reaction is carried out in a solvent, inert inorganic solvents are preferred. It is preferred to use aromatic hydrocarbons such as toluene, xylenes, anisole or tetralin, and aliphatic ethers such as tetrahydrofuran, dimethoxyethane, dioxane or tetrahydropropane. Particularly preferred solvents are toluene and xylenes. It is also possible to use solvent mixtures.

The reaction is preferably carried out without a solvent.

The reaction is preferably carried out at temperatures of 80° C. to 200° C., especially of 20° C. to 180° C. and particularly preferably of 100° C. to 150° C.

The reaction preferably takes place under a conventional inert gas such as nitrogen, helium or argon.

The substituted arylamines are generally formed in good to very good yields, for example of 50 to 99%, by the process according to the invention. When the reaction has ended, the complexes of formula (I) according to the invention used as catalysts can be re-used in another reaction.

EXAMPLES

Example 1

Not According to the Invention

Preparation of diiodo-di-(1-methyl-3-(ethoxycarbonylpropyl)-imidazolin-2-ylidene)-palladium (II)

190 mg of Pd(OAc)$_2$ (1 mmol), 900 mg of NaI (6 mmol), 290 mg of sodium tert-butylate (3 mmol) and 320 mg of 1-methyl-3-(ethoxycarbonylpropyl)-imidazolium bromide (1 mmol) were placed in a Schlenk tube. 20 ml of tetrahydrofuran and 5 ml of ethanol were added by means of a syringe. The reaction vessel was placed in an ultrasound bath for 10 min and the reaction mixture was subsequently stirred for a few hours at 22° C. and then for 14 h at 40° C. The progress of the reaction was monitored by thin layer chromatography (SiO$_2$; methylene chloride/1% methanol). When the reaction had ended, the solvents were distilled off under vacuum and the residue was taken up in methylene chloride and purified by column chromatography (SiO$_2$; methylene chloride/1% methanol).

Example 2

Preparation of diiodo-di-(1-methyl-3-(ethoxycarbonylpropyl)-imidazolin-2-ylidene)-palladium (II) supported on aminomethylpolystyrene/2% divinylbenzene 5 ml of a 2 M solution of triethylaluminium in toluene (0.1 mmol) were added to 100 mg of aminomethylpolystyrene/ 2% divinylbenzene (loading 1 mmol). After a reaction time of 1 h, the supernatant was decanted off and 100 mg of the complex of Example 1 (0.2 mmol) in 10 ml of tetrahydrofuran were added. The reaction mixture was stirred for 16 h, initially at 22° C. and then at 40° C., during which time the supernatant became increasing decolourized while the polymer resin assumed a yellow-brown coloration. The reaction mixture was filtered through a glass frit and the residue was washed with methylene chloride, tetrahydrofuran, methanol, water, dimethylformamide and methanol again, and dried under vacuum.

Example 3

Preparation of 4-anilinobenzonitrile 364 mg of 4-bromobenzonitrile (2 mmol), 205 mg of aniline (2.2 mmol), 231 mg of sodium tert-butylate (2.4 mmol) and 50 mg of the supported complex of Example 2 (0.04 mmol, 2 mol %) were placed in a 20 ml flanged reaction vessel with a magnetic stirrer bead. The vessel was closed with a septum, evacuated and filled with an argon atmosphere. 6 ml of degassed xylene were added by means of a syringe and the mixture was stirred at 120° C. for 16 h. When the reaction had ended, the mixture was extracted by shaking with water/methylene chloride, the catalyst being separated off by filtration of the combined fractions through a glass frit. The organic fractions were dried and analysed by gas chromatography.

Conversion: 70%

Yield of 4-anilinobenzonitrile: 270 mg

Selectivity in respect of 4-anilinobenzonitrile, based on conversion: >90%

Example 4

Preparation of 4-anilinobenzonitrile

The supported complex used in Example 3 was washed with methanol, tetrahydrofuran and diethyl ether and used in another reaction analogous to Example 3.

Conversion: 50%

Yield of 4-anilinobenzonitrile: 190 mg

Selectivity in respect of 4-anilinobenzonitrile, based on conversion: >90%

What is claimed is:

1. A compound of formula (I):

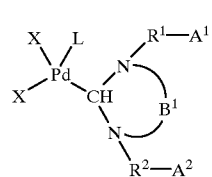

wherein

X is halogen, trifluoromethanesulphonate, acetylacetonate or acetate,

L is a radical of the formula P(D)$_3$, D being alkyl, cycloalkyl, aryl, aralkyl, alkylaryl or heteroaryl, or a radical of the formula N(E)$_2$, E being alkyl, cycloalkyl, aryl, aralkyl, alkylaryl or heteroaryl, or a radical of formula (II):

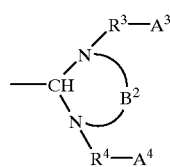

(II)

B¹ and B² are identical or different and are a radical to complete a heterocycle and are selected from one or more radicals have the following formulae:

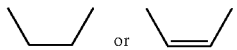

R¹ to R⁴ are identical or different and are a divalent radical from the group selected from the group consisting of alkyl, cycloalkyl, aryl, aralkyl and alkylaryl, and mixtures thereof, each of which is optionally substituted by COO-($C_1$–$C_4$-alkyl), O($C_1$–$C_4$-alkyl) or $CONH_2$, and A¹ to A⁴ are identical or different and are hydrogen or a chemical bond from the group consisting selected from the group consisting of —CONH—, —CO—O—OC—, —COO—, —O— and

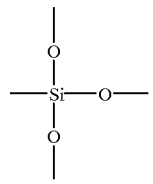

via which the compound is bonded to a support, with the proviso that at least one A is other than hydrogen.

2. The compound according to claim 1, wherein
X is halogen,
L is a radical of the formula P(D)₃, D being a radical seleted from the group consisting of cyclohexyl, phenyl, naphthyl and tolyl, and a radical of formula (II):

(II)

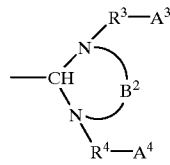

B¹ and B² are identical or different and and are selected from one or more radicals having the following formulae:

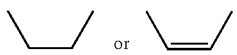

R¹ to R⁴ are identical or different and are a divalent radical from the group selected from the group consisting of alkyl, cycloalkyl, aryl, aralkyl and alkylaryl, each of which is optionally substituted by COO-($C_1$–$C_4$-alkyl), O($C_1$–$C_4$-alkyl) or $CONH_2$, and A¹ to A⁴ are identical or different and are hydrogen or a chemical bond selected from the group consisting of —CONH—, —CO—O—OC—, —COO—, —O— and

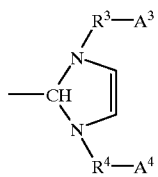

via which the compound is bonded to the support, with the proviso that at least one A is other than hydrogen and the support is selected from inorganic supports and polymeric supports.

3. The compound according to claim 1, wherein
X is I,
L is

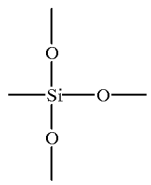

B¹ is

,

R¹ and R³ are identical and are a divalent radical -($C_1$–$C_6$-alkyl)-or —$CH_2$—, R² and R⁴ are identical and are a divalent radical -($C_1$–$C_6$-alkyl)-, —$(CH_2)_3$—, A¹ and A³ are identical and are hydrogen, and A² and A⁴ are identical and are a chemical bond from the group selected from the group consisting of —CONH—, —CO—O—OC—, —COO—, —O— and

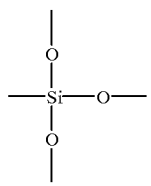

and the support is an inorganic support selected from the group consisting of silica gel, magnesium oxide and aluminum oxide, or a polymeric support from the group comprising polyester, polyether, polyethylene, polypropylene and polystyrene.

4. The compound of claim 3, wherein R² and R⁴ are —$(CH_2)_3$—.

* * * * *